United States Patent
Cui et al.

(10) Patent No.: US 10,738,323 B2
(45) Date of Patent: Aug. 11, 2020

(54) GENERATION OF INDUCED PLURIPOTENT STEM CELLS FROM NORMAL HUMAN MAMMARY EPITHELIAL CELLS

(71) Applicant: Cedars-Sinai Medical Center, Los Angeles, CA (US)

(72) Inventors: Xiaojiang Cui, Arcadia, CA (US); Sareen Dhruv, Porter Ranch, CA (US); Loren A. Ornelas, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 14/904,641

(22) PCT Filed: Jul. 11, 2014

(86) PCT No.: PCT/US2014/046405
§ 371 (c)(1),
(2) Date: Jan. 12, 2016

(87) PCT Pub. No.: WO2015/006725
PCT Pub. Date: Jan. 15, 2015

(65) Prior Publication Data
US 2016/0145642 A1    May 26, 2016

Related U.S. Application Data (60) Provisional application No. 61/845,590, filed on Jul. 12, 2013.

(51) Int. Cl.
| | | |
|---|---|---|
| *C12N 15/85* | (2006.01) | |
| *C12N 5/071* | (2010.01) | |
| *C12N 5/10* | (2006.01) | |
| *C12N 5/074* | (2010.01) | |

(52) U.S. Cl.
CPC .......... *C12N 15/85* (2013.01); *C12N 5/0696* (2013.01); *C12N 15/8509* (2013.01); *C12N 2501/115* (2013.01); *C12N 2501/235* (2013.01); *C12N 2501/415* (2013.01); *C12N 2501/602* (2013.01); *C12N 2501/603* (2013.01); *C12N 2501/604* (2013.01); *C12N 2501/608* (2013.01); *C12N 2501/727* (2013.01); *C12N 2506/09* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 8,183,038 B2 | 5/2012 | Thomson et al. | |
| 8,257,941 B2 | 9/2012 | Sakurada et al. | |
| 8,268,620 B2 | 9/2012 | Thomson et al. | |
| 8,440,461 B2 | 5/2013 | Thomson et al. | |
| 8,546,140 B2 | 10/2013 | Mack et al. | |
| 8,691,574 B2 | 4/2014 | Mack | |
| 8,741,648 B2 | 6/2014 | Rajesh et al. | |
| 8,765,470 B2 | 7/2014 | Thomson et al. | |
| 9,328,332 B2 | 5/2016 | Mack | |
| 9,447,382 B2 | 9/2016 | Mack | |
| 9,499,786 B2 | 11/2016 | Thomson et al. | |
| 2009/0203141 A1* | 8/2009 | Lin ........................ | C12N 15/63 435/456 |
| 2010/0279404 A1* | 11/2010 | Yamanaka ............ | C12N 5/0696 435/366 |
| 2011/0104125 A1* | 5/2011 | Yu .......................... | A61K 35/545 424/93.7 |
| 2011/0200568 A1 | 8/2011 | Ikeda et al. | |
| 2012/0009676 A1 | 1/2012 | Mack | |
| 2012/0196360 A1 | 8/2012 | Okita et al. | |
| 2012/0315697 A1 | 12/2012 | Pettit et al. | |
| 2013/0040302 A1* | 2/2013 | Burke ................... | C12N 5/0696 435/6.12 |
| 2013/0189778 A1 | 7/2013 | Mack | |
| 2013/0217117 A1 | 8/2013 | Thomson et al. | |
| 2014/0057355 A1 | 2/2014 | Thomson et al. | |
| 2014/0134143 A1 | 5/2014 | Baylink et al. | |
| 2014/0315306 A1 | 10/2014 | Tryggvason et al. | |
| 2015/0175973 A1 | 6/2015 | Yamanaka et al. | |
| 2015/0297794 A1* | 10/2015 | Yamashita ............. | A61K 35/44 424/423 |

(Continued)

FOREIGN PATENT DOCUMENTS

| | | | |
|---|---|---|---|
| EP | 3152295 A1 | 4/2017 | |
| WO | 2011016588 A1 | 2/2011 | |

(Continued)

OTHER PUBLICATIONS

Okita et al, A more efficient method to generate integration-free human iPS cells, Nature Methods, vol. 8 No. 5, 2011, 409-414.*
Chou et al., Efficient Human iPS Cell Derivation by a Non-Integrating Plasmid from Blood Cells with Unique Epigenetic and Gene Expression Signatures, Cell Research, vol. 21(3), pp. 518-529.
KnockOut ESC/iPSC Medium Kit, GIBCO Catolog, 2011, Cat Nos. A1411290-01, A14130-01, pp. 1-4.
Lu et al., A Defined Xeno-Free and Feeder-Free Culture System for the Derivation, Expansion and Direct Differentiation of Transgene-Free Patient-Specific Induced Pluripotent Stem Cells, Biomaterial, 2014, vol. 35, pp. 2816-2826.
Okita et al., An Efficient Nonviral Method to Generate Integration-Free Human-Induced Pluripotent Stem Cels from Cord Blood and Peripheral Blood Cells, Stem Cells, 2013, vol. 31, pp. 458-466.

(Continued)

*Primary Examiner* — Maria Marvich
(74) *Attorney, Agent, or Firm* — Nixon Peabody LLP (57) ABSTRACT

Described herein are reprogramming techniques allowing for production of mammary-derived iPSCs ("m-iPSCs"). The m-iPSCs described herein exhibit all the hallmarks of stem cell identity including round cluster, bright colony morphology, clonal expansion, and pluripotent marker expression (alkaline phosphatase expression, Oct-4, nanog, etc.) Further refined techniques allow for generation of m-iPSCs under essentially defined conditions.

15 Claims, 7 Drawing Sheets

(56) References Cited

U.S. PATENT DOCUMENTS

| | | |
|---|---|---|
| 2016/0108369 A1 | 4/2016 | Kuno et al. |
| 2017/0107498 A1 | 4/2017 | Sareen et al. |

FOREIGN PATENT DOCUMENTS

| | | |
|---|---|---|
| WO | 2011056971 A2 | 5/2011 |
| WO | 2011138786 A2 | 11/2011 |
| WO | 2011159684 A3 | 12/2011 |
| WO | 2013009825 A1 | 1/2013 |
| WO | 2013040445 A1 | 3/2013 |
| WO | 2013062140 A1 | 5/2013 |
| WO | 2015006725 A2 | 1/2015 |
| WO | 2015188131 A1 | 12/2015 |
| WO | 2017219000 A1 | 12/2017 |

OTHER PUBLICATIONS

Okita et al., A More Efficient Method to Generate Integration-Free Human iPS Cells, Nature Methods, 2011, vol. 8, pp. 409-412.

Rajesh et al., Human Lymphoblastoid B-cell Lines Reprogrammed to EBV-Free Induced Pluripotent Stem Cells, Blood, 2011, vol. 118(7), pp. 1797-1800.

Stemcell Technologies, Reproducible generation of iPS cells with high quality colony morphology for easy identification and rapid subcloning (Catalog 2013, TeSR TM-E7TM) Retrieved from http://www.stemcell.com/media/files/brochure/BB28069-TeSRE7_Reprogramming_Medium_Human_iPS_Cell_Induction.pdf.

Barrett et al., Reliable Generation of Induced Pluripotent Stem Cells from Human Lymphoblastoid Cell Lines: Reliable iPSC Generation from LCLs, Stem Cells Translational Medicine: SCTM, 2014, vol. 3(12), pp. 1429-1434.

Bayart et al. Technological Overview of iPS Induction from Human Adult Somatic Cells. Current Gene Therapy (2013). 13:73-92.

Choi et al., Reprogramming of EBV-Immortalized B-Lymphocyte Cell Lines into Induced Pluripotent Stem Cells, Blood, 2011, vol. 118(7), pp. 1801-1805.

Ye et al., Hematopoietic Cells as Sources for Patient-Specific iPSCs and Disease Modelling, Cell Cycle, 2011, vol. 10 (17), pp. 2840-2844.

International Search and Written Opinion for International application No. PCT/US2014/046405 dated Nov. 14, 2014 and completed Sep. 29, 2014.

\* cited by examiner

Figure 5.
Alkaline phosphatase

GENERATION OF INDUCED PLURIPOTENT STEM CELLS FROM NORMAL HUMAN MAMMARY EPITHELIAL CELLS

CROSS-REFERENCE TO RELATED APPLICATIONS

This application is a National Phase of International Application No. PCT/US2014/046405, filed Jul. 11, 2014, currently pending, which designated the U.S. and that International Application was published under PCT Article 21(2) in English, which claims priority under 35 U.S.C. § 119(e) to U.S. Provisional Patent Application No. 61/845,590, filed Jul. 12, 2013, the contents of which are herein incorporated by reference in their entirety.

FIELD OF THE INVENTION

Described herein are compositions and methods related to pluripotent stem cells derived from mammary tissue. Such compositions and methods find application in regenerative medicine.

BACKGROUND

There is growing evidence that in many cancers, tumors are initiated maintained by rare populations of dysregulated cells with stem cell-like properties, collectively known as cancer stem cells ("CSCs"). These CSCs possess the hallmark stem cell properties of self-renewal and multipotent differentiation capacity. It is also these same properties of CSCs that promote the pronounced effects of CSCs in cancer disease generation and progression, through initiation of tumor formation, chemoresistance, bulk generation of heterogenous tumor cells, and malignancy. Despite this increasing evidence for the critical role of CSCs in cancer development, the cellular origins of CSCs remains highly obscured and positive identification of mammary CSCs ("maCSCs") in the specific context of breast cancer remains elusive. The picture is even more difficult to ascertain, given that the mere existence of human mammary stem cells ("maSCs") is controversial. This lack of understanding creates highly divergent possibilities of maCSCs arising from endogenous stem cells altered through genetic mutation, or from dedifferentiation of adult somatic cells. Which mechanism accounts for breast cancer pathogenesis remains a totally unanswered question.

Clearly, establishing the existence and identifying the biological characteristics of human maSCs and their progeny would also be a helpful first step in advancing identification of mammary CSCs ("maCSCs") in breast cancer. An improving understanding of breast cancer as subtypes possessing genetic signatures similar to a cell-of-origin, identifying both maSCs and maCSCs would shed light on crucial questions related to mechanisms of stem-cell origin or adult dedifferentiation. Ultimately, identifying the relevant pathological actors and mechanisms of cancer parthenogenesis would allow distinguishing between maSCs, normal mammary gland tissue cells, bulk tumor cells and maCSCs, thereby allowing development of targeted therapeutic approaches for cancer treatment. Present efforts to hone in on maSC or maCSC populations are severely hampered by the fact that primary normal and tumor mammary epithelial cells can only be cultured for short periods of time before they cease proliferating and undergo senescence. Thus, there is a great need in the art for platforms allowing for generation of materials relevant to mammary development and breast cancer formation.

Described herein are induced pluripotent stem cell ("iPSC") related reprogramming techniques allowing for production of mammary-derived iPSCs ("m-iPSCs"). Importantly, the m-iPSCs described herein exhibit all the hallmarks of stem cell identity including round cluster, bright colony morphology, clonal expansion, and pluripotent marker expression (alkaline phosphatase expression, Oct-4, nanog, etc.) Further refined techniques allow for generation of m-iPSCs under essentially defined conditions.

SUMMARY OF THE INVENTION

Described herein is a method of generating human mammary-derived induced pluripotent stem cells (m-iPSCs), including providing a quantity of human mammary cells, transfecting the human mammary cells with at least one vector encoding at least one reprogramming factor, plating the cells on a culture vessel coated with a substrate, and culturing the cells in an induction media, wherein the transfection, plating and culturing generates colonies of human mammary-derived induced pluripotent stem cells (m-iPSCs).

In other embodiments, the mammary cells are from primary cells. In other embodiments, the mammary cells are from a tumor. In other embodiments, the mammary cells are from a cell line. In other embodiments, the at least one vector encodes at least one reprogramming factor selected from the following group: Oct4, Sox2, Nanog, Kruppel-like Factor 4 (KLF4), L-Myc, Lin28, SV40 Large T Antigen (SV40LT) and p53 shRNA. In other embodiments, the at least one vector is an episomal vector. In other embodiments, the episomal vector is an oriP/EBNA1 vector. In other embodiments, transfecting mammary cell includes nucleofection or lipofection. In other embodiments, plating the cells on a culture vessel coated with a substrate further includes culturing in norm oxygen conditions. In other embodiments, the substrate is Matrigel. In other embodiments, the induction media includes one or more of the following compounds: HA-100, CHIR99021, PD0325901, and A83-01. In other embodiments, culturing the cells in an induction media is for a period of 10-31 days.

Also described herein is composition of m-iPSCs produced by the method including providing a quantity of human mammary cells, transfecting the human mammary cells with at least one vector encoding at least one reprogramming factor, plating the cells on a culture vessel coated with a substrate, and culturing the cells in an induction media, wherein the transfection, plating and culturing generates colonies of human mammary-derived induced pluripotent stem cells (m-iPSCs). In other embodiments, the m-iPSCs are capable of serial passaging as a cell line. In other embodiments, a multi-potent cell is produced by culturing the composition of m-iPSCs capable of serial passaging as a cell line in the presence of a differentiation agent.

Further described herein is a method of reprogramming a human mammary cell, including providing a quantity of human mammary cells, culturing the human mammary cells in the presence of at least one vector and/or at least one reprogramming agent, plating the cells on a culture vessel coated with a substrate, and culturing the cells in an induction media, wherein the transfection, plating and culturing reprograms the human cell to a less differentiated state. In other embodiments, the mammary cells are from primary cells. In other embodiments, the mammary cells are from a tumor. In other embodiments, the mammary cells are from a cell line. In other embodiments, the at least one vector encodes at least one reprogramming factor including Oct4, Sox2, Nanog, Kruppel-like Factor 4 (KLF4), L-Myc, Lin28, SV40 Large T Antigen (SV40LT) and p53 shRNA. In other embodiments, the at least one vector encodes at least one reprogramming factor includes a microRNA. In other embodiments, the at least one reprogramming agent is a small molecule including HA-100, PD0325901, SB431542, CHIR99021, A83-01 and/or Y-27632.

BRIEF DESCRIPTION OF THE DRAWINGS

FIG. 1. Reprogramming of mammary cells into m-iPSC colonies. As shown, human mammary epithelial cells from primary cultures retain individual cell, or small aggregate morphology after nucleofection (Day 1). Clusters of cells begin to form (Day 4) with elongated fibroblast-like morphology appearing (Day 6). These cells begin to possess a distinct stem cell colony-like formation cluster morphology (Day 10), with bright, compact colonies being visible thereafter (Day 13). Cells can be further cultured with retention of stem-like morphology (Day 21).

FIG. 2. Reprogrammed m-iPSC colonies express pluripotent markers. As shown in phase contrast, m-iPSCs possess the characteristic bright, compact colony morphology, with Alkaline Phosphatase (AP)-FITC staining clearly displaying expression of high levels of AP. Overlay of fluorescent and phase contrast image is shown, showing a high number of efficiently reprogrammed m-iPSC cell within colonies.

FIG. 3. Picking m-iPSCs colonies. Individual colonies of reprogrammed m-iPSCs were isolated and expanded. Various examples are shown, including at lower and high magnification. In such examples, colonies possess the bright, round morphology of stem cells, along with a high cystoplasm-to-nucleus ratio.

FIG. 4. Clonal expansion of m-iPSCs colonies. Additional example of identifying cells for clonal expansion are shown. As reprogramming is not 100% efficient, individual cells were identified based on morphology, and clonally expanded as described.

DETAILED DESCRIPTION

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: The Science and Practice of Pharmacy 22$^{nd}$ ed., Pharmaceutical Press (Sep. 15, 2012); Hornyak et al., Introduction to Nanoscience and Nanotechnology, CRC Press (2008); Singleton and Sainsbury, Dictionary of Microbiology and Molecular Biology 3$^{rd}$ ed., revised ed., J. Wiley & Sons (New York, N.Y. 2006); Smith, March's Advanced Organic Chemistry Reactions, Mechanisms and Structure 7$^{th}$ ed., J. Wiley & Sons (New York, N.Y. 2013); Singleton, Dictionary of DNA and Genome Technology 3$^{rd}$ ed., Wiley-Blackwell (Nov. 28, 2012); and Green and Sambrook, Molecular Cloning: A Laboratory Manual 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, Antibodies A Laboratory Manual 2$^{nd}$ ed., Cold Spring Harbor Press (Cold Spring Harbor N.Y., 2013); Köhler and Milstein, Derivation of specific antibody-producing tissue culture and tumor lines by cell fusion, Eur. J. Immunol. 1976 July, 6(7):511-9; Queen and Selick, Humanized immunoglobulins, U.S. Pat. No. 5,585,089 (1996 December); and Riechmann et al., Reshaping human antibodies for therapy, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As described, a chief limitation in studies relating to isolation and identification of mammary stem cells ("maSCs") and mammary cancer stem cells ("maCSCs") is a lack of source material, given that primary mammary cell cultures rapidly reach senescence. Reprogramming techniques related to induced pluripotent stem cells ("iPSCs") allows a new avenue of approach by allowing for generation of a renewal source material of mammary cells for study. Reprogramming techniques related to generation iPSCs have been established a variety of cell types ranging from fibroblasts to neurons. Nevertheless, despite this apparent extensibility across different cells, there have not been reports of successful techniques applicable to mammary cells. What is known is that the INK4/ARF locus, which is active in primary mammary cells, is a barrier to reprogramming. The INK4/ARF genetic locus encodes for several factors, including p15INK4B (also known as CDKN2B), p16INK4A (also known as CDKN2A) and ARF, which positively regulate the p53 and retinoblastoma tumour suppressor pathways to inhibit cell proliferation and promote cellular senescence. In this regard, it may be understood that not all somatic cell sources for reprogramming are created equal, and mammary cells may possess barriers preventing their successful reprogramming and dedifferentiation. In any case, generation of iPSCs, regardless of tissue source would necessarily possess the hallmark properties of self-renewal, and pluripotency as demonstrated by expansion capacity, pluripotent marker expression (e.g., alkaline phosphatase, Oct-4, nanog, Sox-2, etc.) and multi-lineage tumorigenesis in immunocompromised animals (e.g., SCID mouse) establishing differentiation into various progeny.

Generally, different approaches for reprogramming somatic cells can include integrative, or integration-defective viral delivery, episomal delivery, direct RNA delivery, direct protein delivery, chemical induction and combinations of these features. As described further herein, the adoption of episomal vectors allows for generation of iPSCs substantially free of the vectors used in their production, as episomal or similar vectors do not encode sufficient viral genome sufficient to give rise to infection or a replication-competent virus. At the same time, these vectors do possess a limited degree of self-replication capacity in the beginning somatic host cells. This self-replication capacity provides a degree of persistent expression understood to be beneficial in allowing the dedifferentiation process to initiate take hold in a target host cell.

One example of a plasmid vector satisfying these criteria includes the Epstein Barr oriP/Nuclear Antigen-1 ("EBNA1") combination, which is capable of limited self-replication and known to function in mammalian cells. As containing two elements from Epstein-Barr virus, oriP and EBNA1, binding of the EBNA1 protein to the virus replicon region oriP maintains a relatively long-term episomal presence of plasmids in mammalian cells. This particular feature of the oriP/EBNA1 vector makes it ideal for generation of integration-free iPSCs.

More specifically, persistent expression of reprogramming factor encoded in an oriP/EBNA1 vector occurs across multiple cell divisional cycles. Sufficiently high levels of reprogramming factors across several cell divisions allows for successful reprogramming even after only one infection. While sustained expression of reprogramming factors is understood to be beneficial during initial programming stages, otherwise unlimited constitutive expression would hamper subsequent stages of the reprogramming process. For example, unabated expression of reprogramming factors would interfere with subsequent growth, development, and fate specification of the host cells.

At the same time, a further benefit is the eventual removal of the reprogramming factor transgenes, as a small portion of episomes is lost per cell cycle. This is due to the asymmetric replication capacity of the host cell genome and episomal self-replication and it is estimated that approximately 0.5% of vector is lost per generation. Gradual depletion of plasmids during each cell division is inevitable following propagation leading to a population of integration-free iPSCs. The persistent, yet eventual abrogation of reprogramming factor expression on oriP/EBNA1 is highly coincident with the needs for different stages of the reprogramming process and eliminates the need for further manipulation steps for excision of the reprogramming factors, as has been attempted through use of transposons and excisable polycistronic lentiviral vector elements. Although oriP/EBNA1 has been applied by others in reprogramming studies, the reported efficiencies are extremely low (as few as 3 to 6 colonies per million cells nucleofected), which may be due, in-part, to reliance on large plasmids encoding multiple reprogramming factors (e.g., more than 12 kb), negatively impacting transfection efficiency.

In addition to these choices in vector designs, the specific combinations of reprogramming factors implemented in the literature have varied. As mentioned, reprogramming factors that have been used include pluripotency-related genes Oct-4, Sox-2, Lin-28, Nanog, Sall4, Fbx-15 and Utf-1. These factors are traditionally understood to be expressed early during development and are involved in the maintenance of the pluripotent potential of a subset of cells that will constituting the inner cell mass of the pre-implantation embryo and post-implantation embryo proper. Their ectopic expression of is believed to allow the establishment of an embryonic-like transcriptional cascade that initates and propagates an otherwise dormant endogenous core pluripotency program within a host cell. Certain other reprogramming determinants, such as Tert, Klf-4, c-Myc, SV40 Large T Antigen ("SV40LT") and short hairpin RNAs targeting p53 ("shRNA-p53") have been applied. There determinants may not be potency-determining factors in and of themselves, but have been reported to provide advantages in reprogramming. For example, TERT and SV40LT are understood to enhance cell proliferation to promote survival during reprogramming, while others such as short hairpin targeting of p53 inhibit or eliminate reprogramming barriers, such as senescence and apoptosis mechanisms. In each case, an increase in both the speed and efficiency of reprogramming is observed. In addition, microRNAs ("miRNAs") are also known to influence pluripotency and reprogramming, and some miRNAs from the miR-290 cluster have been applied in reprogramming studies. For example, the introduction of miR-291-3p, miR-294 or miR-295 into fibroblasts, along with pluripotency-related genes, have also been reported to increase reprogramming efficiency.

While various vectors and reprogramming factors in the art appear to present multiple ingredients capable of establishing reprogramming in cells, a high degree of complexity occurs when taking into account the stoichiometric expression levels necessary for successful reprogramming to take hold. For example, somatic cell reprogramming efficiency is reportedly fourfold higher when OCT-4 and SOX2 are encoded in a single transcript on a single vector in a 1:1 ratio, in contrast to delivering the two factors on separate vectors. The latter case results in a less controlled uptake ratio of the two factors, providing a negative impact on reprogramming efficiency. One approach towards addressing these obstacles is the use of polycistronic vectors, such as inclusion of an internal ribosome entry site ("IRES"), provided upstream of transgene(s) that is distal from the transcriptional promoter. This organization allows one or more transgenes to be provided in a single reprogramming vector, and various inducible or constitutive promoters can be combined together as an expression cassette to impart a more granular level of transcriptional control for the plurality of transgenes. These more specific levels of control can benefit the reprogramming process considerably, and separate expression cassettes on a vector can be designed accordingly as under the control of separate promoters.

Although there are advantages to providing such factors via a single, or small number of vectors, upper size limitations on eventual vector size do exist, which can stymie attempts to promote their delivery in a host target cell. For example, early reports on the use of polycistronic vectors were notable for extremely poor efficiency of reprogramming, sometimes occurring in less than 1% of cells, more typically less than 0.1%. These obstacles are due, in-part, to certain target host cells possessing poor tolerance for large constructs (e.g., fibroblasts), or inefficient processing of IRES sites by the host cells. Moreover, positioning of a factor in a vector expression cassette affects both its stoichiometric and temporal expression, providing an additional variable impacting reprogramming efficiency. Thus, some improved techniques can rely on multiple vectors each encoding one or more reprogramming factors in various expression cassettes. Under these designs, alteration of the amount of a particular vector for delivery provides a coarse, but relatively straightforward route for adjusting expression levels in a target cell.

In some instances, there may be further benefits in altering the chemical and/or atmospheric conditions under which reprogramming will take place. For example, as the pre-implantation embryo is not vascularized and hypoxic (similar to bone marrow stem-cell niches) reprogramming under hypoxic conditions of 5% $O_2$, instead of the atmospheric 21% O2, may further provide an opportunity to increase the reprogramming efficiency. Similarly, chemical induction techniques have been used in combination with reprogramming, particularly histone deacetylase (HDAC) inhibitor molecule, valproic acid (VPA), which has been found wide use in different reprogramming studies. At the same time, other small molecules such as MAPK kinase (MEK)-ERK ("MEK") inhibitor PD0325901, transforming growth factor beta ("TGF-β") type I receptor ALK4, ALK5 and ALK7 inhibitor SB431542 and the glycogen synthase kinase-3 ("GSK3") inhibitor CHIR99021 have been applied for activation of differentiation-inducing pathways (e.g. BMP signaling), coupled with the modulation of other pathways (e g inhibition of the MAPK kinase (MEK)-ERK pathway) in order to sustain self-renewal. Other small molecules, such as Rho-associated coiled-coil-containing protein kinase ("ROCK") inhibitors, such as Y-27632 and thiazovivin ("Tzv") have been applied in order to promote survival and reduce vulnerability of pSCs to cell death, particularly upon single-cell dissociation. Finally, in some instances, techniques such as nucleofection allow for enhanced transfer directly into the cell nucleus and the cytoplasm, without relying on cell division for the transfer of DNA into the nucleus.

Further, in some instances, various sub-combinations of reprogramming factors, chemical and/or atmospheric conditions described herein may be deployed to reprogram, but not dedifferentiate somatic mammary cells into a fully pluripotent state. For example, while it is understood that generation of m-iPSCs in some instances may possess useful properties for recapitulation of maSC and maCSC candidate phenotypes, reprogramming resulting in incomplete, partial, or aberrant reprogramming not resulting in acquisition of pluripotency may further prove to be useful in reprogramming somatic mammary cells directly into maSCs or maCSC candidate phenotypes. Such approaches may be described as conditional reprogramming, transformation, or other terms understood in the art. But in any case, such an approach avoids the need for recapitulation, and may be regarded as a means for direct conversion of mammary somatic cells into possible maSC and maCSC candidates.

Following successful reprogramming, clonal selection allows for generation of pluripotent stem cell lines. Ideally, such cells possess requisite morphology (i.e., compact colony, high nucleus to cytoplasm ratio and prominent nucleolus), self-renewal capacity for unlimited propagation in culture (i.e., immortal), and with the capability to differentiate into all three germ layers (e.g., endoderm, mesoderm and ectoderm). Further techniques to characterize the pluripotency of a given population of cells include injection into an immunocompromised animal, such as a severe combined immunodeficient ("SCID") mouse, for formation of teratomas containing cells or tissues characteristic of all three germ layers.

In addition to the choice of delivery vectors, reprogramming factor combinations, and conditions for reprogramming, further variations must consider the nature of the host target cell for reprogramming. As described, a wide variety of cells have served as sources for reprogramming including fibroblasts, stomach and liver cell cultures, human keratinocytes, adipose cells, and frozen human monocyte. There appears to be a wide and robust potential for dedifferentiation across many tissues sources. Nevertheless, it is widely understood that depending on the donor cell type, reprogramming is achieved with different efficiencies and kinetics. For example, although fibroblasts remain the most popular donor cell type for reprogramming studies, other types of cells such as human primary keratinocytes transduced with Oct-4, Sox-2, Klf-4 and c-Myc have been reported to reprogram 100 times more efficiently and two-fold faster. Additionally, some other cell types, such as cord blood cells, may only require a subset of reprogramming factors, such as Oct-4 and Sox-2 for dedifferentiation to take hold, while neural progenitor cells may only require Oct-4. Without being bound to any particular theory, it is believed that differences in reprogramming efficiency and/or reprogramming factor requirements of specific host cells result from high endogenous levels of certain reprogramming factors and/or intrinsic epigenetic states that are more amenable to reprogramming.

Importantly, it is generally understood that tissue-specific iPSC lines also possess subtle differences resulting from the specific cell-of-origin. These properties are colloquially referred to "parental memory". This aspect of tissue-specific cells is believed to arise, in-part, from differences in epigenetic methylation status, divergent telomeric lengths, which can manifest themselves in lineage preference, or other structural and functional alterations upon differentiation. Extending these techniques, disease-specific iPSCs can also be generated from adult cells that harbor genetic mutations or other alterations, thereby providing a useful model of cellular development for understanding disease initiation and progression. Together, iPSC technology provides an alternative approach for identification of mammary gland development by creation of mammary-derived iPSCs. These cells can then be recapitulated into maSCs, maCSCs, and various cellular intermediates generated during mammary gland development or as a model for breast cancer disease.

It is notable that few, if any, studies report iPSC generation from mammary cells, indicating possible difficulty in deriving iPSCs from this tissue type. Even within the single tissue type of mammary cells, it is noted that primary mammary cell cultures may pose specific challenges or properties that are different from cells in an established mammary cell lines. For example, it is known that widely studied breast cell lines such as, non-tumor initiating MCF10 contain depleted INK4/ARF locus. MCF10 cells are therefore more amenable to reprogramming compared to primary cultures, considering the barrier function of this particular genetic locus as involved in p53-related senescence. Similarly, other cell lines such as MCF7 are more susceptible for neoplastic transformation than primary mammary cell cultures or MCF10. This adds a dimension wherein MCF7 may be highly compatible with iPSC generation (based on extand replicative and differentiation capacity) and subsequent differentiation capacity mirroring maCSC generation based on other translocations and/or parental memory in that particular cell line. It may be considered that primary mammary cell cultures represent a more accurate representation of normal mammary cell function and development, as lacking technical artifacts persistent in established mammary cell lines. Choice of iPSC generation from primary mammary cell cultures or specific mammary cell lines may rest on the eventual application of interest, although for the reasons described above, such primary mammary cell culture may prove to be the most difficult cells to reprogram and dedifferentiate.

Described herein is a composition including a culture of mammary-derived iPSCs ("m-iPSCs"). In certain embodiments, the m-iPSCs are derived from a somatic cell via reprogramming. In certain embodiments, the human mammary cell is from a primary culture of cells, a biopsy sample isolated from a human subject, such as normal healthy tissue and/or solid tumor tissue. In certain embodiments, the human mammary cell is a basal/myoepithelial or luminal cell. In other embodiments, the human mammary cell is from a cell line, such as MCF7 or MCF10.

In different embodiments, reprogramming includes applications of reprogramming factors, including one or more of following: Oct4, Sox2, Klf4, c-Myc, Lin28, SV40-LT, p53 short hairpin RNA ("shRNA"), and nanog. In different embodiments, the reprogramming factors are encoded by a vector. In different embodiments, the vector can be, for example, a non-integrating episomal vector, plasmid, retrovirus (integrating and non-integrating) and/or other genetic elements known to one of ordinary skill. In different embodiments, the vector encodes one or more reprogramming factors, and combinations of vectors can be used together to deliver one or more of Oct4, Sox2, Klf4, c-Myc, Lin28, SV40-LT, p53 shRNA and nanog. For example, oriP/EBNA1 is an episomal vector that can encode a vector combination of multiple reprogramming factors, such as pCXLE-hUL, pCXLE-hSK, pCXLE-hOCT3/4-shp53-F, and pEP4 EO2S T2K.

In various embodiments, one can reprogram human mammary epithelial cells ("HMECs") via plasmid nucleofection of combinations of oriP/EBNA1 based vectors pCXLE-hUL, pCXLE-hSK, pCXLE-hOCT3/4-shp53-F, and pEP4 EO2S T2K plasmid vectors. In some reprogramming methods, sub-combinations of these vectors are used. In various embodiments, 0.1 µg to 0.5 µg, 0.5 µg to 1 µg, 1 µg to 2.5 µg, 2.5 µg to 5 µg, or 5 µg or more of each plasmid is used. 1.5 µg per plasmid After nucleofection, cells can be on a substrate coated dish, such as Matrigel, and fed with Mammary Epithelium Basal/myoepithelial Medium ("MEBM"). In certain embodiments, norm-oxygen conditions (e.g., 5% $O_2$) during reprogramming may aid efficiency of the reprogramming. Other examples of norm-oxygen conditions includes less than 10%, 9%, 8%, 7%, 6%, 5%, 4%, 3%, 2% $O_2$ or less. Cells in MEBM are cultured for 48 h and gradually changed to Reprogramming Medium ("RM") consisting of DMEM/F12, 1% Glutamax, 1% NEAA, 1% N2, 2% B27, 1% antibiotic-antifungal, 0.1 mM beta-mercaptoethanol, 100 ng/mL basic fibroblast growth factor (bFGF), and 1000 units/mL human Leukemia Inhibitory Factor (hLIF). An alternative RM formulation includes 64 mg/L L-Ascorbic Acid, 19.4 mg/L insulin, 100 µg/L FGF, 10.7 mg/L transferrin, 14 µg/L sodium, selenite, and 543 mg/L $NaHCO_3$ with volume up to 1 L of DMEM/F12 media. It is understood that such components can be at variable concentrations depending on the desired application, such as less than 1 mg/L, 1-10 mg/L, 10 mg/L to 50 mg/L, 50 mg/L to 100 mg/L, 100 mg/L to 250 mg/L, 250 mg/L or more of a media component. In other embodiments, small molecules can be added to RM to enhance reprogramming efficiency. Such small molecules include components of a modified "3i" medium, composed of: 1) HA-100 (10 µM), 2) glycogen synthase kinase 3β inhibitor of the Wnt/β-catenin signaling pathway (CHIR99021, 3 µM), 3) MEK pathway inhibitor (PD 0325901, 0.5 µM), 4) Selective inhibitor of TGF-β type I receptor ALK5 kinase, type I activin/nodal receptor ALK4 and type I nodal receptor ALK7 (A 83-01, 0.5 µM). Other possible small molecules include histone deacetylase (HDAC) inhibitor molecule, valproic acid (VPA), MAPK kinase (MEK)-ERK ("MEK") inhibitors, transforming growth factor beta ("TGF-β") type I receptor ALK4, ALK5 and ALK7 inhibitor SB431542, glycogen synthase kinase-3 ("GSK3") inhibitors, Rho-associated coiled-coil-containing protein kinase ("ROCK") inhibitors, such as Y-27632 and thiazovivin ("Tzv") In various embodiments, concentrations of these small molecules can range from 0.1 µM to 0.25 µM, 0.25 µM to 0.5 µM, 0.5 µM to 1 µM, 1 µM to 5 µM, 5 µM-10 µM, 10 µM to 15 µM, 15 µM to 20 µM, or 20 µM or more. Finally, colonies with ES/iPSC-like morphology would appear at days 25, 26, 27, 28, 29, 30, or 31 post-nucleofection. In different embodiments for which partial, conditional reprogramming is of interest, other types of reprogrammed cells can appear at different time periods, such as before 14, 15, 16, 17, 18, 19, 20, 21, 22, 23, 24 day post-nucleofection.

In various embodiments, HMECs are cultured in MEBM in a T-75 flask until cells reached approximately 90% confluence. Reprogramming of the HMECs was achieved by plasmid nucleofection, performed using oriP/EBNA1 based pCXLE-hUL, pCXLE-hSK, pCXLE-hOCT3/4-shp53-F, and pEP4 EO2S T2K plasmid vectors and Amaxa Human Dermal Fibroblast Nucleofector Kit. HMECs ($1\times10^6$ cells per nucleofection) were harvested and centrifuged at 200 g for 5 minutes. The cell pellet was re-suspended carefully in Nucleofector Solution (VPD-1001, Lonza) and combined with episomal plasmids (1.5 µg per plasmid) expressing, Oct4, Sox 2, Klf4, c-Myc, Lin28, SV40LT and p53 shRNA. The cell/DNA suspension was transferred into the Nucleofector® and the E-010 program applied. Immediately after nucleofection, cells were plated on BD Matrigel coated dishes and fed with MEBM. All cultures were be maintained under norm-oxygen conditions (5% $O_2$) during reprogramming, which further enhances the efficiency of iPS cell generation. The media was kept on for 48 h and gradually changed to RM consisting of DMEM/F12, 1% Glutamax, 1% NEAA, 1% N2, 2% B27, 1% antibiotic-antifungal, 0.1 mM beta-mercaptoethanol, 100 ng/mL basic fibroblast growth factor (bFGF), and 1000 units/mL human Leukemia Inhibitory Factor (hLIF). In other embodiments, small molecules can be added to RM to enhance reprogramming efficiency. An alternative RM formulation includes 64 mg/L L-Ascorbic Acid, 19.4 mg/L insulin, 100 µg/L FGF, 10.7 mg/L transferrin, 14 µg/L sodium, selenite, and 543 mg/L $NaHCO_3$. In addition, small molecules were supplemented in the RM to enhance reprogramming efficiency. The small molecules used were, 1) HA-100 (10 µM), 2) glycogen synthase kinase 3β inhibitor of the Wnt/β-catenin signaling pathway (CHIR99021, 3 µM), 3) MEK pathway inhibitor (PD 0325901, 0.5 µM), 4) Selective inhibitor of TGF-β type I receptor ALK5 kinase, type I activin/nodal receptor ALK4 and type I nodal receptor ALK7 (A 83-01, 0.5 µM). Fresh RM was added daily to the conditioned media. This was repeated daily for the next 4 days. On the 7th day post nucleofection, all medium was aspirated from the wells and cells were fed with RM. Media was changed every 3rd day to fresh RM for the next 13 days (day 20 post nucleofection).

In other embodiments, the reprogramming factors are delivered by techniques known in the art, such as nuclefection, transfection, transduction, electrofusion, electroporation, microinjection, cell fusion, among others. In other embodiments, the reprogramming factors are provided in a cellular extract of a pluripotent stem cell. In various embodiments, the m-iPSCs are capable of differentiating into mammary stem cells ("maSCs") candidates. In other embodiments, the m-iPSCs are capable of differentiating into mammary cancer stem cells ("maCSCs") candidates. In various embodiments, the m-iPSCs possess features of pluripotent stem cells. Some exemplary features of pluripotent stem cells including differentiation into cells of all three germ layers (ectoderm, endoderm, mesoderm), either in vitro or in vivo when injected into an immunodeficient animal, expression of pluripotency markers such as Oct4, Sox2, nanog, TRA-1-60, TRA-1-81, SSEA4, high levels of alkaline phosphatase ("AP") expression, indefinite propagation in culture, among other features recognized and appreciated by one of ordinary skill.

Establishment of m-iPSC cell lines provides an in vitro model that could be used for recapitulating the formation of candidate maSCs. In alternative embodiments, reprogramming allows for direct conversion into candidate maSCs. A key challenge is that relatively little is known about the ontology of maSCs during embryonic development. Milk lines are the first visible embryonic mammary gland structures arising from migration of cells from the embryonic ectoderm. Therefore, various ligands or other factors influencing ectoderm fate-specification, such as manipulation of Notch, Wnt, bone morphogenetic protein ("BMP"), and fibroblast growth factor ("FGF") signaling pathways can be applied to promote ectodermal cell lineage development from m-iPSCs, these differentiated cells providing a population for which to generate populations of maSC candidates. For example, overexpression of BMP antagonist, Noggin, is known to lead to defects in ectodermal organ development, Notch pathway signaling prevents differentiation into alternative fates by promoting ectodermal development, and FGFs are essential regulators of the specification of the ectodermal stem cells from the ventral skin to form mammary placodes during embryogenesis.

Studies using growth factor cocktail combinations can be supplemented by heterotopic tissue recombination assays in order to replicate aspects of the complex tempo-spatial events that occur during embryogenesis. For example, m-iPSCs can be cultured in the presence of mammary mesenchyme and/or mammary epithelium in order to promote generation of candidate maSCs. Under any of these approaches, generation of candidate maSC candidate populations is followed by further characterization of stem-cell like properties. As described, several different types of possible maSC populations and mammary progenitor cells in the human breast can possess varying degrees of stem cell-like properties. This is due, in-part, to the functional complexity of the breast in mammalian development. The breast is unlike most veterbrate organs that are structured during embryongenesis and maintain their basic form throughout an organisms life. Instead, mammary gland development includes distinct chains of events related to embryogenesis (bud development, generation of mammary fat pad, luminal formation), puberty (formation of ductal network and terminal end buds), and pregnancy (expansion of ductal tree and differentiation into lobular alveoli with secretory epithelium). The primitive cell types in the breast provide the expansion and differentiation capacity behind these events, thereby accounting for the existence of multiple maSC populations and progenitor cells. A key obstacle presented by the existence of this myriad of cells is their relatively similar marker expression profile. For example, it has been suggested that luminal progenitor cells are Lin$^-$ CD29$^{lo}$CD49f$^-$CD61$^+$Kit$^+$, whereas alveolar epithelial cells are suggested to be Lin$^-$ CD29$^{lo}$CD49f$^-$CD61$^-$, and myoepithelial cells are suggested to be Lin$^-$ CD29$^{hi}$CD49f$^{hi}$CD24$^1$CD61$^-$. This small divergence in marker expression amongst different cells provides limited analytical resolution.

Similarly, generation of candidate maCSCs from m-iPSCs, or direct conversion of mammary somatic cells into candidates maCSCs, can be achieved by exploiting the oncgogenic properties of CSCs. For example, application of anticancer chemotherapeutic compounds such as Taxol or Actinomycin D can be applied as a selection factor to select for chemoresistant maCSCs. Alternatively, culturing of m-iPSCs in the presence of carcinoma cultured media has been reported to induced CSC-like phenotype in mouse maSCs, and a similar approach can be adapted for human m-iPSCs. Further, given that CSCs are widely understood to result from dysregulation of stem cell-related pathways, perturbation of m-iPSCs to cause transformation into maCSCs can be explored. An alternative approach can rely on overexpression of pluripotency markers such as Oct4, Sox 2, and nanog, or relying on a cell source including high potential for transformation, such as MCF7 cell line. Candidate maCSCs can be characterized for biochemical and functional properties using the following described techniques. For example, certain CSC markers, such as CD133$^-$ and ALDH1$^+$ have been identified as common among CSCs from several different cancer diseases, and such markers can provide an initial screen for generation of mammary-specific CSCs. In addition, increasing understanding of breast cancer has demonstrated via genetic signatures that certain subtypes as possess features in common with different cells-of-origin. These same genetic signatures for subtypes such as claudin-low or nomal-breast-like can then be used as a mechanism to screen various maCSCs generated by the described method, thereby establishing a link between the generated maCSCs and features of not only breast cancer, but specific breast cancer subtypes.

Further functional studies for confirming maCSC identity can include exposure to anticancer Taxol or Actinomycin D as a measure of chemoresistance, or ionizing radiation. Moreover, a variety of tumor sphere formation or invasion assays are well-known in the art, and such methods can be applied in establishing the functional properties of the generated maCSCs and subsequent roles in breast cancer development.

Also described herein is a method of producing m-iPSCs, or a method of reprogramming somatic mammary cells. In certain embodiments, the method includes providing a quantity of human mammary cells, reprogramming the mammary cells using one or more vectors, each vector encoding one or more reprogramming factors. In some embodiments, the method includes further culturing the reprogrammed mammary cells to produce an m-iPSC cell. In other embodiments, methods allows for direct conversion into a candidate maSC or candidate maCSC. In certain embodiments, the human mammary cell is from a primary culture of cells, a biopsy sample isolated from a human subject, such as normal healthy tissue and/or solid tumor tissue. In certain embodiments, the human mammary cell is a basal/myoepithelial or luminal cell. In other embodiments, the human mammary cell is from a cell line, such as MCF7 or MCF10. In different embodiment, the one or more vectors include use of oriP/EBNA1 based vector. In other embodiments, reprogramming the mammary cells using one or more vectors, each vector encoding one or more reprogramming factors can include examples such as pCXLE-hUL, pCXLE-hSK, pCXLE-hOCT3/4-shp53-F, and pEP4 EO2S T2K. In different embodiments, reprogramming the mammary cells using one or more vectors includes use of nucleofection. In certain embodiments, mammary cells are treated with sodium butyrate to improve m-iPSC yield. In a different embodiment, further culturing the reprogrammed mammary cells to produce a m-iPSC cell includes culturing on a tissue culture vessel coated with a substrate, such as extracellular matrix (ECM) or Matrigel coated dishes. In other embodiments, the reprogramming and/or further culturing is under norm-oxygen conditions, such as 1, 2, 3, 4, 5, 6, 7, 8, 9, 10, 11, 12, 13, 14, 15, 16, 17, 18, 19, or 20% $O_2$. In another embodiment, reprogramming and/or further culturing includes use of an induction media. In certain embodiments, the induction media includes a one or more of the following: an inhibitor of MYLK, PKA, and PKC pathways, an inhibitor the Wnt/β-catenin signaling pathways, such as an inhibitor of glycogen synthase kinase 3β an inhibitor of MEK pathway, and an inhibitor of TGF-β pathways, such as type I receptor ALK5 kinase, type I activin/nodal receptor ALK4 and type I nodal receptor ALK7. For example, an exemplary combination of inhibitors in an induction media can include HA-100 (MYLK, PKA, and PKC pathways inhibitor), CHIR99021 (GSK3 inhibitor), PD0325901 (MEK inhibitor) and/or A83-01 (TGF-β inhibitor). In different embodiments, further culturing with induction media is for 1, 2, 3, 4, 5, 6, 7, 8, 9, 10, 11, 12 days or more after nucleofection. In different embodiments, further culturing the reprogrammed mammary cells is for a total culture period of 9, 10, 11, 12, 13, 14, 15, 16, 17, 18, 19, 20, 21, 22, 23, 24, 25, 26, 27, 28, 29, 30, 30 days or more.

In various embodiments, one can reprogram human mammary epithelial cells ("HMECs") via plasmid nucleofection of combinations of oriP/EBNA1 based vectors pCXLE-hUL, pCXLE-hSK, pCXLE-hOCT3/4-shp53-F, and pEP4 EO2S T2K plasmid vectors. In some reprogramming methods, sub-combinations of these vectors are used. In various embodiments, 0.1 µg to 0.5 µg, 0.5 µg to 1 µg, 1 µg to 2.5 µg, 2.5 µg to 5 µg, or 5 µg or more of each plasmid is used. 1.5 µg per plasmid After nucleofection, cells can be on a substrate coated dish, such as Matrigel, and fed with Mammary Epithelium Basal/myoepithelial Medium ("MEBM"). In certain embodiments, norm-oxygen conditions (e.g., 5% $O_2$) during reprogramming may aid efficiency of the reprogramming. Other examples of norm-oxygen conditions includes less than 10%, 9%, 8%, 7%, 6%, 5%, 4%, 3%, 2% $O_2$ or less. Cells in MEBM are cultured for 48 h and gradually changed to Reprogramming Medium ("RM") consisting of DMEM/F12, 1% Glutamax, 1% NEAA, 1% N2, 2% B27, 1% antibiotic-antifungal, 0.1 mM beta-mercaptoethanol, 100 ng/mL basic fibroblast growth factor (bFGF), and 1000 units/mL human Leukemia Inhibitory Factor (hLIF). An alternative RM formulation includes 64 mg/L L-Ascorbic Acid, 19.4 mg/L insulin, 100 µg/L FGF, 10.7 mg/L transferrin, 14 µg/L sodium, selenite, and 543 mg/L $NaHCO_3$ with volume up to 1 L of DMEM/F12 media. It is understood that such components can be at variable concentrations depending on the desired application, such as less than 1 mg/L, 1-10 mg/L, 10 mg/L to 50 mg/L, 50 mg/L to 100 mg/L, 100 mg/L to 250 mg/L, 250 mg/L or more of a media component. In other embodiments, small molecules can be added to RM to enhance reprogramming efficiency. Such small molecules include components of a modified "3i" medium, composed of: 1) HA-100 (10 µM), 2) glycogen synthase kinase 3β inhibitor of the Wnt/β-catenin signaling pathway (CHIR99021, 3 µM), 3) MEK pathway inhibitor (PD 0325901, 0.5 µM), 4) Selective inhibitor of TGF-β type I receptor ALK5 kinase, type I activin/nodal receptor ALK4 and type I nodal receptor ALK7 (A 83-01, 0.5 µM). Other possible small molecules include histone deacetylase (HDAC) inhibitor molecule, valproic acid (VPA), MAPK kinase (MEK)-ERK ("MEK") inhibitors, transforming growth factor beta ("TGF-β") type I receptor ALK4, ALK5 and ALK7 inhibitor SB431542, glycogen synthase kinase-3 ("GSK3") inhibitors, Rho-associated coiled-coil-containing protein kinase ("ROCK") inhibitors, such as Y-27632 and thiazovivin ("Tzv") In various embodiments, concentrations of these small molecules can range from 0.1 µM to 0.25 µM, 0.25 µM to 0.5 µM, 0.5 µM to 1 µM, 1 µM to 5 µM, 5 µM-10 µM, 10 µM to 15 µM, 15 µM to 20 µM, or 20 µM or more. Finally, colonies with ES/iPSC-like morphology would appear at days 25, 26, 27, 28, 29, 30, or 31 post-nucleofection. In different embodiments for which partial, conditional reprogramming is of interest, other types of reprogrammed cells can appear at different time periods, such as before 14, 15, 16, 17, 18, 19, 20, 21, 22, 23, 24 day post-nucleofection.

In various embodiments, HMECs are cultured in MEBM in a T-75 flask until cells reached approximately 90% confluence. Reprogramming of the HMECs was achieved by plasmid nucleofection, performed using oriP/EBNA1 based pCXLE-hUL, pCXLE-hSK, pCXLE-hOCT3/4-shp53-F, and pEP4 EO2S T2K plasmid vectors and Amaxa Human Dermal Fibroblast Nucleofector Kit. HMECs ($1 \times 10^6$ cells per nucleofection) were harvested and centrifuged at 200 g for 5 minutes. The cell pellet was re-suspended carefully in Nucleofector Solution (VPD-1001, Lonza) and combined with episomal plasmids (1.5 µg per plasmid) expressing, Oct4, Sox 2, Klf4, c-Myc, Lin28, SV40LT and p53 shRNA. The cell/DNA suspension was transferred into the Nucleofector® and the E-010 program applied. Immediately after nucleofection, cells were plated on BD Matrigel coated dishes and fed with MEBM. All cultures were be maintained under norm-oxygen conditions (5% $O_2$) during reprogramming, which further enhances the efficiency of iPS cell generation. The media was kept on for 48 h and gradually changed to RM consisting of DMEM/F12, 1% Glutamax, 1% NEAA, 1% N2, 2% B27, 1% antibiotic-antifungal, 0.1 mM beta-mercaptoethanol, 100 ng/mL basic fibroblast growth factor (bFGF), and 1000 units/mL human Leukemia Inhibitory Factor (hLIF). In other embodiments, small molecules can be added to RM to enhance reprogramming efficiency. An alternative RM formulation includes 64 mg/L L-Ascorbic Acid, 19.4 mg/L insulin, 100 µg/L FGF, 10.7 mg/L transferrin, 14 µg/L sodium, selenite, and 543 mg/L $NaHCO_3$. In addition, small molecules were supplemented in the RM to enhance reprogramming efficiency. The small molecules used were, 1) HA-100 (10 µM), 2) glycogen synthase kinase 3β inhibitor of the Wnt/β-catenin signaling pathway (CHIR99021, 3 µM), 3) MEK pathway inhibitor (PD 0325901, 0.5 µM), 4) Selective inhibitor of TGF-β type I receptor ALK5 kinase, type I activin/nodal receptor ALK4 and type I nodal receptor ALK7 (A 83-01, 0.5 µM). Fresh RM was added daily to the conditioned media. This was repeated daily for the next 4 days. On the 7th day post nucleofection, all medium was aspirated from the wells and cells were fed with RM. Media was changed every 3rd day to fresh RM for the next 13 days (day 20 post nucleofection).

Further described herein is a composition including a culture of mammary stem cell candidates ("maSCs"). In various embodiments, the candidate maSCs originate from a luminal or basal/myoepithelial compartment, or both. In other embodiments, the culture of maSCs were generated from a primary culture of cells, a biopsy sample isolated from a human subject, such as normal healthy tissue and/or solid tumor tissue. In certain embodiments, the human mammary cell is a basal/myoepithelial or luminal cell. In other embodiments, the human mammary cell is from a cell line, such as MCF7 or MCF10. In various embodiments, the maSCs express the following panel of markers: CD1d, CD10, CD24, CD29, CD49, CD61, CD133, epithelial cell adhesion molecule (EpCAM), Lin, Muc-1, Thy-1. In other embodiments, the maSCs express Oct4, Sox2, nanog, TRA-1-60, TRA-1-81, SSEA4. In different embodiments, the maSCs can be differentiated luminal progenitors, luminal cells, basal/myoepithelial progenitors, basal/myoepithelial cells, myoepithelial progenitors, myoepithelial cells. In various embodiments, the maSCs are capable of forming a mammary gland from a single cell. In other embodiments, the maSCs are capable of repopulating a compartment of a mammary gland, such as basal/myoepithelial or luminal compartments of a host subject.

Also described herein a method of generating a population of candidate maSCs, including providing a quantity of human m-iPSCs, and inducing the formation of candidate maSCs. In different embodiments, inducing the formation of candidate maSCs include use of ligands or other factors influencing ectoderm fate-specification. This includes, for example, ligands or other factors related to Notch, Wnt, bone morphogenetic protein ("BMP"), and fibroblast growth factor ("FGF") signaling pathways. In another embodiment, inducing the formation of maSCs include co-culture with a cell layer. This include, for example, culturing m-iPSCs in the presence of mammary mesenchyme and/or mammary epithelium.

Further described herein is a composition including a culture of mammary cancer stem cells ("maCSCs") candidates. In various embodiments, the candidate maCSCs originate from a luminal or basal/myoepithelial compartment, or both. In other embodiments, the culture of maCSCs were generated from a primary culture of cells, a biopsy sample isolated from a human subject, such as normal healthy tissue and/or solid tumor tissue. In certain embodiments, the human mammary cell is a basal/myoepithelial or luminal cell. In certain embodiments, the human mammary cell is a basal/myoepithelial or luminal cell. In other embodiments, the human mammary cell is from a cell line, such as MCF7 or MCF10. In different embodiments, maCSCs may express one or more markers such as one or more of following: ALDH1A (also known as ALDH1A1), CD24, CD44, CD45, CD90, CD105, CD117, CD133, CD166, EpCAM, ESA, ABCB5, ABCG2, SCA, Snail, Slug and SOX2. For example, a mCSC may express CD44$^+$/CD24$_{low}$ or CD73$^-$ CD90$^+$. In other embodiments, mCSCs possess nuclear localization of developmental pathway related molecules, thereby demonstrating activation of proteins such as Gli1 (hedgehog signaling), Notch1 (Notch signaling), and/or β-Catenin (Wnt signaling). In other embodiments, maCSCs possess activation of TGF-β-related pathways, such as activation of SMAD signaling proteins, such as Smad1, Smad3 and Smad5. In other embodiments, maCSCs are capable of forming tumors composed of multilineage cells in vivo. This can include formation of tumor tissues when injected in an immunosuppressed, or immunodeficient mouse. In other embodiments, the maCSCs possess a molecular signature similar to subsets of breast cancer, including luminal A, luminal B, luminal C, molecular-apocrine, basal/myoepithelial, or normal-breast-like cancer. In other embodiments, maCSCs possess a molecular signature similar to subsets of breast cancer, such as ER$^1$Her2$^1$, ER$^1$Her2$^-$, ER$^-$Her2$^1$, and ER$^-$Her2$^-$. In other embodiments, the CSCs are resistant to an anticancer drug such as Taxol, Fulvestant. and Actinomycin D. In other embodiments, the maCSCs are resistant to ionizing radiation.

Also described herein a method of generating a population of candidate maCSCs, including providing a quantity of human m-iPSCs, and inducing the formation of maCSCs. In other embodiments, the method includes inducing the formation of maSCs. In other embodiments, inducing the formation of maCSCs include application of anticancer chemotherapeutic compounds such as Taxol or Actinomycin as a selection factor. In other embodiments, inducing the formation of maCSCs includes exposure to ionizing or carcinoma cultured media. In other embodiments, inducing the formation of maCSCs includes application of reprogramming factors, such as Oct4, Sox 2, and nanog.

EXAMPLE 1

Generation of Human Mammary Epithelial Cell-Derived iPSCs Using Episomal Plasmids Generally, the inventors adapted reported iPSCs reprogramming techniques to produce mammary-derived iPSCs ("m-iPSCs"). Certain modifications include, for example, nucleofection of a specific 5 plasmid combination each encoding one or more specific reprogramming factors, and modified "3i" pluripotency media to establish the reprogrammed m-iPSC cultures.

Figure 1:
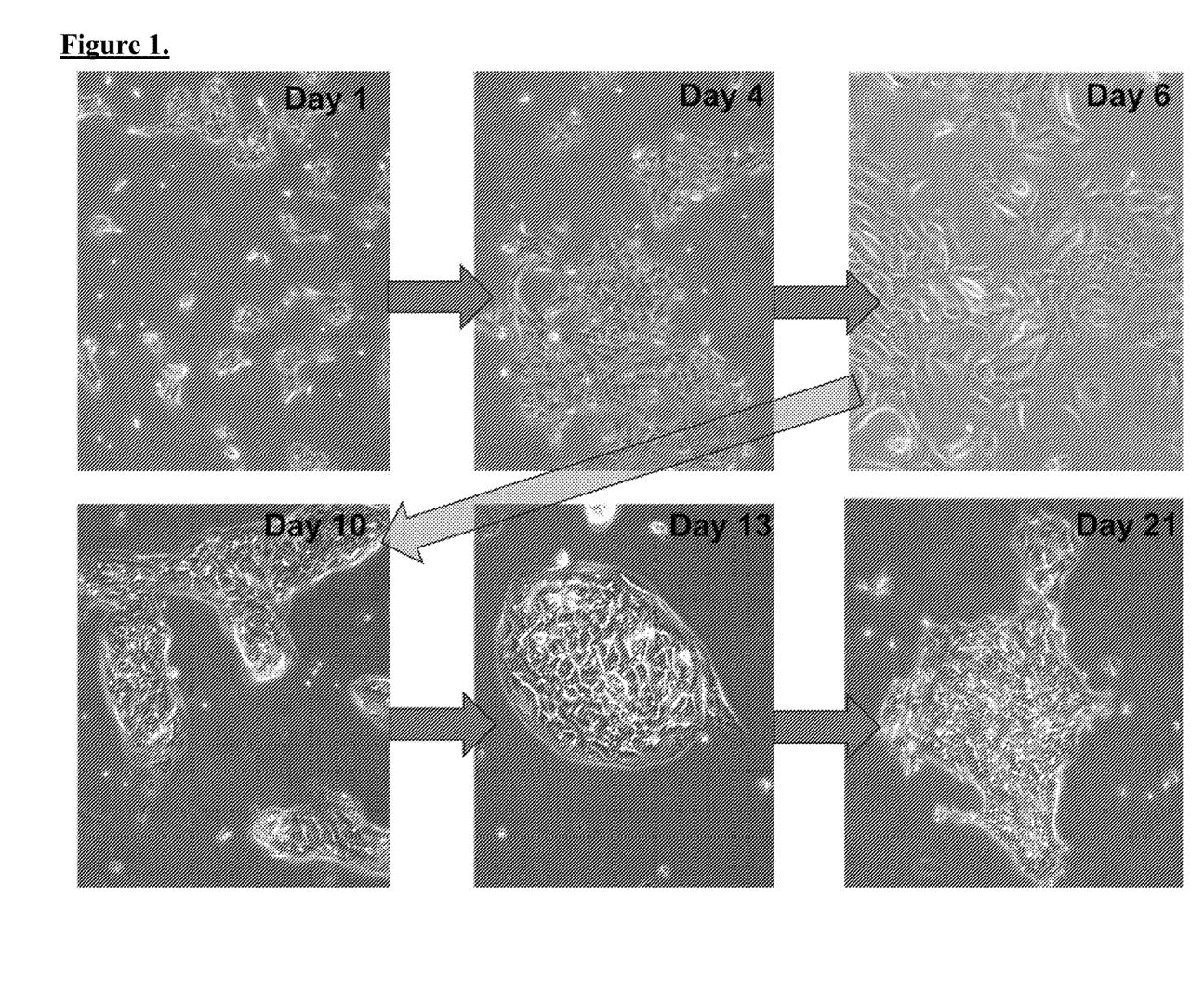
Figure 2:
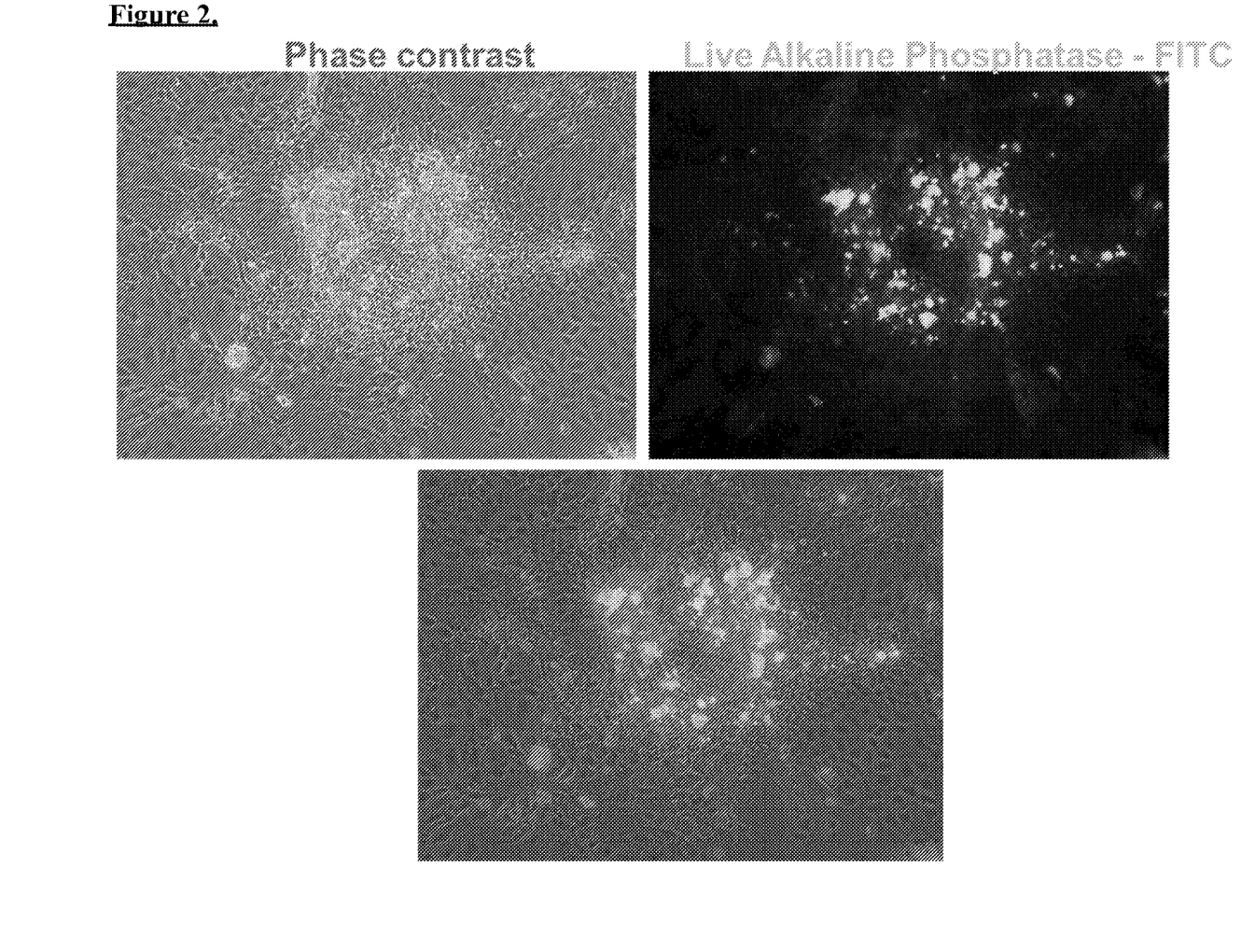

Briefly, reprogramming of the HMECs was achieved by plasmid nucleofection of oriP/EBNA1 based pCXLE-hUL, pCXLE-hSK, pCXLE-hOCT3/4-shp53-F, and pEP4 EO2S T2K plasmid vectors. Unlike viral transduction, these genes do not integrate and are instead expressed episomally (extrachromosomal) in a transient fashion. After nucleofection, cells were plated on BD Matrigel coated dishes, fed with Mammary Epithelium Basal/myoepithelial Medium ("MEBM"), and maintained under norm-oxygen conditions (5% $O_2$) during reprogramming. Subsequently, small molecules were supplemented in the Reprogramming Medium ("RM") to enhance reprogramming efficiency, including modified "3i" medium, composed of: 1) HA-100 (10 µM), 2) glycogen synthase kinase 3β inhibitor of the Wnt/β-catenin signaling pathway (CHIR99021, 3 µM), 3) MEK pathway inhibitor (PD 0325901, 0.5 µM), 4) Selective inhibitor of TGF-β type I receptor ALK5 kinase, type I activin/nodal receptor ALK4 and type I nodal receptor ALK7 (A 83-01, 0.5 µM). Finally, colonies with ES/iPSC-like morphology would appear at day 25-31 post-nucleofection. Exemplary differences in cell morphology undergoing reprogramming are shown in FIG. 1, colonies of m-iPSCs expressing alkaline phosphatase are shown in FIG. 2.

EXAMPLE 2

Nucleofection Using Non-Integrating Episomal Vectors

Human mammary epithelial cells (HMECs, obtained from ATCC) were cultured in MEBM in a T-75 flask until cells reached approximately 90% confluence. Reprogramming of the HMECs was achieved by plasmid nucleofection, performed using oriP/EBNA1 based pCXLE-hUL, pCXLE-hSK, pCXLE-hOCT3/4-shp53-F, and pEP4 EO2S T2K plasmid vectors (Addgene). Amaxa Human Dermal Fibroblast Nucleofector Kit was utilized to make the virus-free iPSC lines. This method has a significant advantage over viral transduction, because genes do not integrate and are instead expressed episomally (extrachromosomal) in a transient fashion. Briefly, HMECs (1×10$^6$ cells per nucleofection) were harvested and centrifuged at 200 g for 5 minutes. The cell pellet was re-suspended carefully in Nucleofector Solution (VPD-1001, Lonza) and combined with episomal plasmids (1.5 μg per plasmid) expressing, Oct4, Sox 2, Klf4, c-Myc, Lin28, SV40LT and p53 shRNA. The cell/DNA suspension was transferred into the Nucleofector® and the E-010 program applied.

EXAMPLE 3

Induction of Stem Cell Pluripotency

Immediately after nucleofection, cells were plated on BD Matrigel coated dishes and fed with MEBM. All cultures were be maintained under norm-oxygen conditions (5% $O_2$) during reprogramming, which further enhances the efficiency of iPS cell generation. The media was kept on for 48 h and gradually changed to reprogramming media consisting of DMEM/F12, 1% Glutamax, 1% NEAA, 1% N2, 2% B27, 1% antibiotic-antifungal, 0.1 mM beta-mercaptoethanol, 100 ng/mL basic fibroblast growth factor (bFGF), and 1000 units/mL human Leukemia Inhibitory Factor (hLIF). In addition, small molecules were supplemented in the RM to enhance reprogramming efficiency. The small molecules used were, 1) HA-100 (10 μM), 2) glycogen synthase kinase 3β inhibitor of the Wnt/β-catenin signaling pathway (CHIR99021, 3 μM), 3) MEK pathway inhibitor (PD 0325901, 0.5 μM), 4) Selective inhibitor of TGF-β type I receptor ALK5 kinase, type I activin/nodal receptor ALK4 and type I nodal receptor ALK7 (A 83-01, 0.5 μM). Fresh RM was added daily to the conditioned media. This was repeated daily for the next 4 days. On the 7th day post nucleofection, all medium was aspirated from the wells and cells were fed with RM. Media was changed every 3rd day to fresh RM for the next 13 days (day 20 post nucleofection).

EXAMPLE 4

Generation of iPSC Colonies

Figure 3:
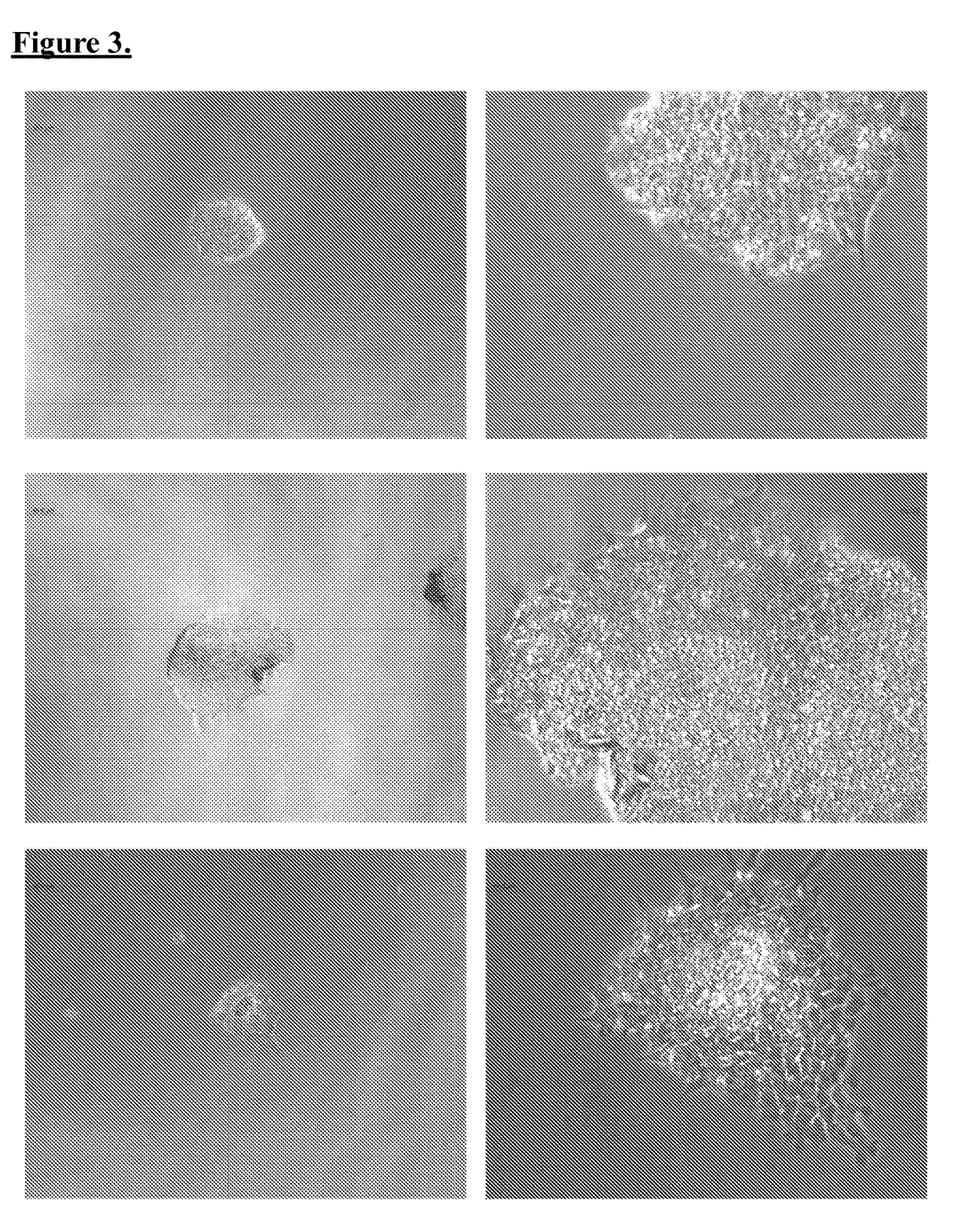
Figure 4:
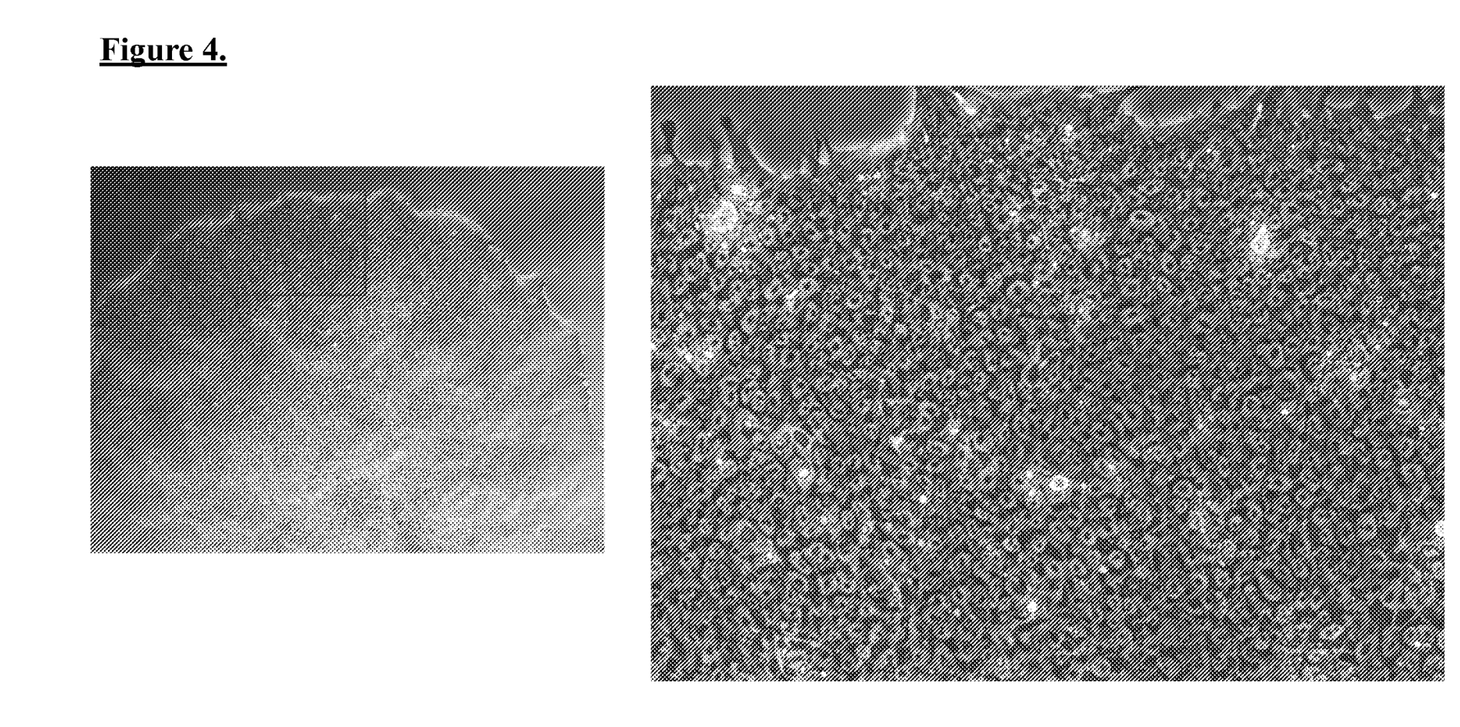

Colonies with ES/iPSC-like morphology appeared at day 25-31 post-nucleofection. Subsequently, colonies with the best morphology were picked on day 31 and transferred to BD Matrigel™ Matrix for feeder-independent maintenance of hiPSCs in chemically-defined mTeSR® 1 medium. Examples of hMEC-iPSC colonies are shown in FIG. 3. hMEC-iPSC colonies display bright morphology, high cytoplasm to nucleus ratio as shown in FIG. 4.

Figure 5:
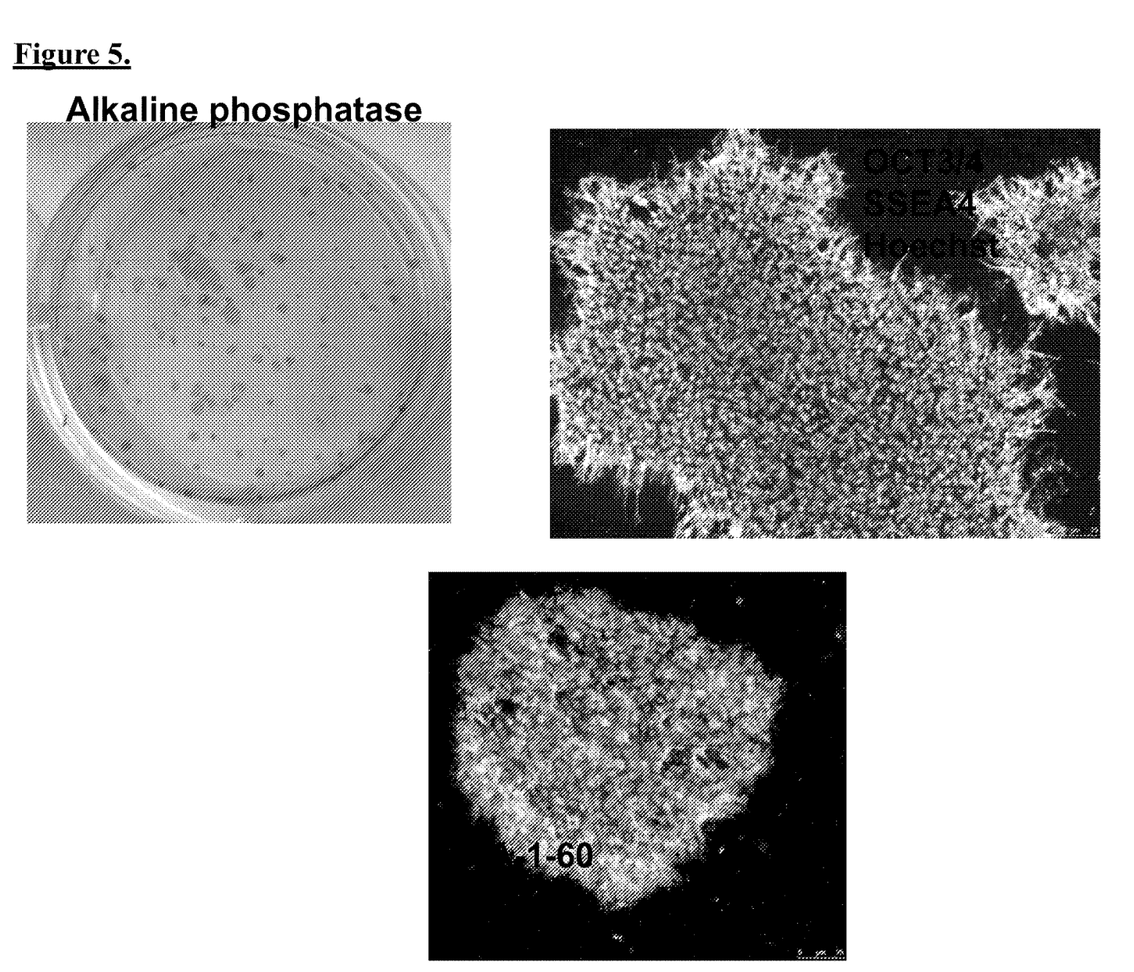
FIG. 5. Pluripotent marker expression of m-iPSCs cells. Cell line CS01i-MECn1 (Clone 1) could successfully be maintained and passaged in culture without loss of pluripotent marker expression. In this example, colonies of plated m-iPSCs expressed pluripotent markers, Oct4, Nanog, SSEA, Tra-1-60, and AP.
Figure 6:
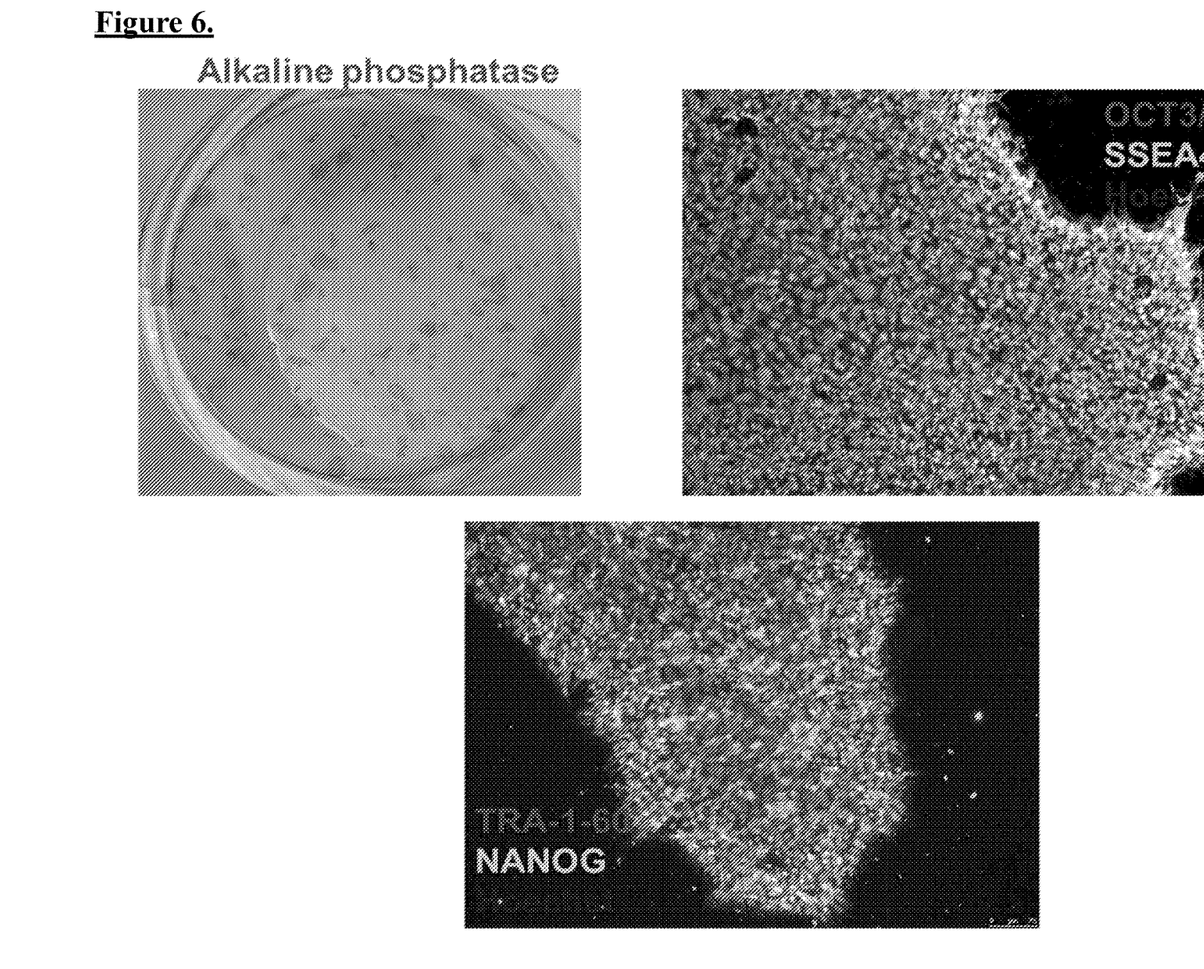
FIG. 6. Pluripotent marker expression of m-iPSCs cells. Cell line CS01i-MECn4 (Clone 4) could successfully be maintained and passaged in culture without loss of pluripotent marker expression. In this example, colonies of plated m-iPSCs expressed pluripotent markers, Oct4, Nanog, SSEA, Tra-1-60, and AP.
Figure 7:
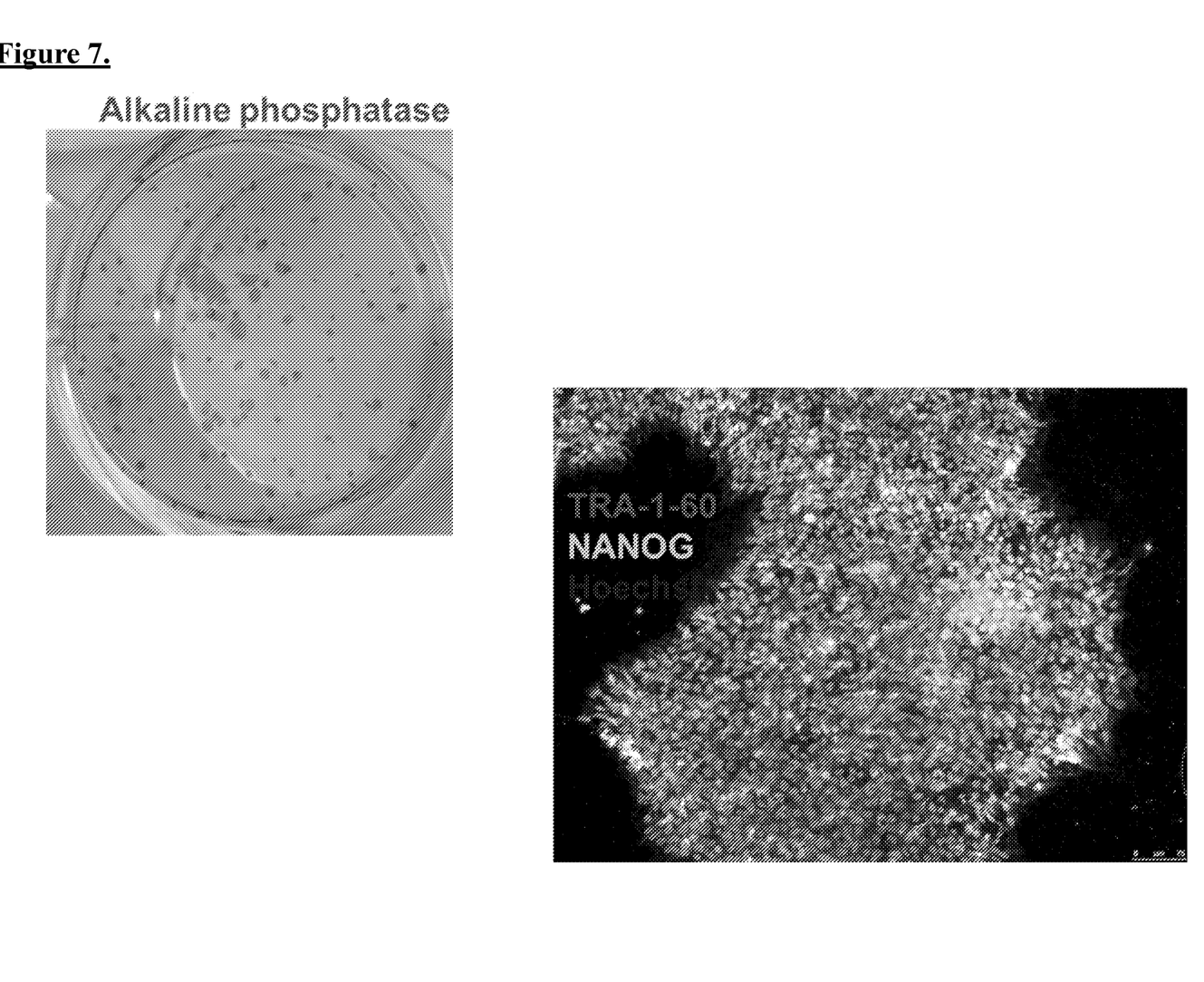
FIG. 7. Pluripotent marker expression of m-iPSCs cells. Cell line CS01i-MECn6 (Clone 6) could successfully be maintained and passaged in culture without loss of pluripotent marker expression. In this example, colonies of plated m-iPSCs expressed pluripotent markers, Nanog, Tra-1-60, and AP.

Six independent iPS cell clones were picked, further expanded and cryopreserved. Three colonies are shown and are designated CS01i-MECn1 (Clone 1), CS01i-MECn4 (Clone 4), and CS01i-MECn6 (Clone 6) are shown in FIGS. 5, 6, and 7, respectively. Each cell line expressed alkaline phosphatase, Oct4, nanog, SSEA4 and/or TRA-1-60 markers as shown.

EXAMPLE 5

Generation of iPSC Colonies Under Essentially Defined Conditions

Extending the above studies, the Inventors have derived suitable media conditions which are essentially defined as shown in Table 1. Application of the above media composition during reprogramming achieves the same results, with reduced growth factor complexity.

TABLE 1

Essentially Defined Media Conditions

|  | Stock | suggested concentration for 1 L | amount needed to make 100 ml |
| --- | --- | --- | --- |
| DMEM/F12 |  | 1 L | 100 ml |
| L-Ascorbic Acid | 5 G | 64 mg/L | 6.4 mg |
| Insulin | 10 mg/ml | 19.4 mg/L | 194 μl |
| FGF | 100 ug/ml | 100 μg/L | 100 μl |
| Transferrin | 50 mg | 10.7 mg/L | 1.07 mg |
| Sodium selenite | 10 G | 14 μg/L | 0.0014 mg |
| NaHCO3 | 500 G | 543 mg/L | 54.3 mg |

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are sources of mammary-derived stem cells, method of detecting biomarkers, prognostic and/or diagnostic panels that include mammary-derived stem cells and their differentiated progeny, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of generating human mammary-derived induced pluripotent stem cells (m-iPSCs), the method comprising:
   providing human mammary cells in culture;
   transfecting the human mammary cells with vectors encoding Oct4, Sox2, Nanog, Kruppel-like Factor 4 (KLF4), L-Myc, Lin28, SV40 Large T Antigen (SV40LT) and p53 shRNA;
   plating the transfected cells on a culture vessel coated with a substrate; and
   culturing the plated cells in an induction media, wherein the transfecting, the plating and the culturing generates colonies of the human m-iPSCs, wherein the induction media comprises HA-100, CHIR99021, PD0325901, and A83-01, wherein the plating of the transfected cells on the culture vessel coated with the substrate further comprises culturing in norm oxygen conditions, and wherein the plated mammary cells express the transfected Oct4, Sox2, Nanog, KLF4, L-Myc, Lin28, SV40LT and p53 shRNA.

2. The method of claim 1, wherein the mammary cells are primary cells.

3. The method of claim 1, wherein the mammary cells are obtained from a tumor.

4. The method of claim 1, wherein the mammary cells are obtained from a cell line.

5. The method of claim 1, wherein the vectors are episomal vectors.

6. The method of claim 5, wherein the episomal vectors are oriP/EBNA1 vectors.

7. The method of claim 1, wherein the transfecting of the mammary cells comprises nucleofection or lipofection.

8. The method of claim 1, wherein the substrate comprises Matrigel.

9. The method of claim 1, wherein the induction media comprises HA-100, CHIR99021, PD0325901, A83-01 and Y-27632.

10. The method of claim 1, wherein the culturing the cells in the induction media is for a period of 10-31 days.

11. A method of reprogramming a human mammary cell, the method comprising:
    providing human mammary cells in culture;
    expanding the human mammary cells to about 90% confluence;
    transfecting the human mammary cells with vectors encoding Oct4, Sox2, Nanog, Kruppel-like Factor 4 (KLF4), L-Myc, Lin28, SV40 Large T Antigen (SV40LT) and p53 shRNA;
    plating the transfected cells on a culture vessel coated with a substrate; and
    culturing the plated cells in an induction media, wherein the expanding, the transfecting, the plating and the culturing reprograms the human mammary cells to a less differentiated state, wherein the induction media comprises HA-100, CHIR99021, PD0325901, and A83-01, wherein the plating of the transfected cells on the culture vessel coated with the substrate further comprises culturing in norm oxygen conditions, and wherein the plated mammary cells express the transfected Oct4, Sox2, Nanog, KLF4, L-Myc, Lin28, SV40LT and p53 shRNA.

12. The method of claim 11, wherein the mammary cells are primary cells.

13. The method of claim 11, wherein the mammary cells are obtained from a tumor.

14. The method of claim 11, wherein the mammary cells are obtained from a cell line.

15. The method of claim 11, wherein the induction media comprises HA-100, PD0325901, SB431542, CHIR99021, A83-01 and Y-27632.

* * * * *